United States Patent [19]  
Taniguchi et al.

[11] Patent Number: 4,692,622  
[45] Date of Patent: Sep. 8, 1987

[54] INFRARED ANALYZER

[75] Inventors: Harutaka Taniguchi; Takafumi Fumoto, both of Kanagawa, Japan

[73] Assignees: Fuji Electric Co., Ltd.; Fuji Electric Corporate Research and Development Ltd., both of Kanagawa, Japan

[21] Appl. No.: 803,967

[22] Filed: Dec. 3, 1985

[30] Foreign Application Priority Data

Dec. 4, 1984 [JP] Japan ................. 59-255900

[51] Int. Cl.[4] .......................................... G01N 21/37
[52] U.S. Cl. .................. 250/343; 250/344; 250/345
[58] Field of Search ............. 250/345, 344, 343; 356/437

[56] References Cited

U.S. PATENT DOCUMENTS

| | | | |
|---|---|---|---|
| 2,924,713 | 2/1960 | Liston | 250/252.1 |
| 3,171,027 | 2/1965 | Wallack | 250/343 |
| 3,770,974 | 11/1973 | Fertig | 250/344 |
| 3,940,623 | 2/1976 | Hempowitz et al. | 250/343 |
| 3,952,196 | 4/1976 | Larsen | 250/372 |
| 3,968,369 | 7/1976 | Luft | 250/344 |
| 4,271,124 | 6/1981 | Speeter | 422/68 |
| 4,336,453 | 6/1982 | Imaki et al. | 250/344 |

FOREIGN PATENT DOCUMENTS 195438 10/1985 Japan ................. 250/343

Primary Examiner—Janice A. Howell  
Assistant Examiner—Constantine Hannaher  
Attorney, Agent, or Firm—Finnegan, Henderson, Farabow, Garrett and Dunner

[57] ABSTRACT

An infrared analyzer where infrared radiation is passed through a measurement cell containing a material that includes a component that absorbs infrared radiation. The radiation exiting the measurement cell passes into a first detector, through an optical filter to a second infrared radiation detector. By analyzing the outputs from each detector and by knowing the characteristics of the optical filter, the concentration of certain infrared absorbing components in the material can be determined.

6 Claims, 13 Drawing Figures

INFRARED ANALYZER

BACKGROUND OF THE INVENTION

The present invention relates to a means for detecting infrared radiation and analyzing materials thereby.

In general, infrared analyzers can be classified into two groups, double-beam type infrared analyzers and single-beam type infrared analyzers. FIG. 2 shows the arrangement of a typical double-beam infrared gas analyzer, and FIG. 3 shows the arrangement of a typical single-beam infrared gas analyzer. As conducive to a full understanding of this invention, the operating principle of an infrared gas analyzer will be described with reference to FIGS. 2 and 3.

As shown in FIG. 2, a light source 2 is provided in a light source chamber 1. The light source 2 emits infrared rays. The infrared rays are divided by a partition chamber 3 into a measurement beam IM and a reference beam IV which are equal in the amount of light in the beam (hereafter light flux). The measurement beam IM is sent into a measurement cell 4, and the reference beam IV is sent into a reference cell 5. A material to be measured, namely, a gas 100 which contains a first component is introduced through a conduit 6 into the measurement cell 4. On the other hand, a gas such as nitrogen gas having no infrared ray absorbing characteristic is sealed in the reference cell 5. The measurement beam IM is subjected to absorption by the first component, and therefore its optical intensity is decreased in accordance with the density of the first component. On the other hand, the optical intensity of the reference beam IV is maintained unchanged, because the reference beam IV is not absorbed. The measurement beam IM and the reference beam IV which have passed through the measurement cell 4 and the reference cell 5, respectively, are applied to gas-sealed detector 8. The second detecting chamber 10 is filled with the gas which is the same as the first component. The measurement beam IM is applied to the first detecting chamber 9, while the reference beam IV is applied to the second detecting chamber 10 which is filled with the gas which is the same as the first component. The gas in the first detecting chamber 9, and the gas in the second detecting chamber 10 absorb the measurement beam IM and the reference beam IV, respectively. Therefore, the gases in the first and second detecting chambers 9 and 10 are heated to different temperatures according to the intensities of the measurement beam IM and the reference beam IV, respectively. The detecting chambers 9 and 10 communicate with each other through a conduit 11. Wire heating elements 12 and 13 are arranged at the middle of the conduit 11 in such a manner that they are thermally coupled to each other. The elements 12 and 13 together with two external resistors (not shown) form a bridge circuit, and are heated by a power source to a temperature higher than the ambient temperature. As the gases in the detecting chambers 9 and 10 are heated by the measurement beam IM and the reference beam IV, respectively, the gases in the detecting chambers 9 and 10 expand, as a result of which a gas flow occurs in the conduit 11 with a flow rate corresponding to the density of the first component in the gas 100. The flow rate is converted into an electrical signal by the elements 12 and 13. A rotor 14 is provided between the detector 8 and cells 4 and 5. The rotor 14 is rotated by a motor M, to periodically intercept the measurement beam IM and the reference beam IV which are applied to the detector 8. FIG. 2 depicts a trimmer 15 for adjusting the light quantities of the beams IM and IV so that they are equal to each other at all times; and 16, 17, 18, 19, 21, 22, and 23 are light transmitting windows.

An amount of optical energy $\Delta I_1$ absorbed in the first detecting chamber 9, and an amount of optical energy $\Delta I_2$ absorbed in the second detecting chamber 10 can be expressed by the following equations (1) and (2), respectively:

$$\Delta I_1 = IM\exp(-\alpha CL)\{1-\exp(-\alpha C_O L_1)\} \quad (1)$$

$$\Delta I_2 = Ir\cdot\{1-\exp(-\alpha C_O L_1)\} \quad (2)$$

Where L is the length of the measurement cell, $L_1$ is the optical path length of the measurement cell, $\alpha$ is the absorption coefficient of the first component gas, $C_O$ is the density of the gas sealed in the detector; C is the first component gas density, Im is the measurement cell incident light flux and Ir is the reference cell incident light flux.

The pressure increments $\Delta P_1$ and $\Delta P_2$ of the first and second detecting chambers 9 and 10 are proportional to $\Delta I_1/V$ and $\Delta I_2/V$ (where V is the volume of each of the first and second detecting chambers 9 and 10).

Therefore, $$\Delta P_2 - \Delta P_1 \propto Ir - Im\cdot\exp(-\alpha CL) \quad (3)$$

The trimmer 15 is operated to adjust the light quantities so that $Im = Ir = I_O$, then $$\Delta P_2 - \Delta P_1 \propto I_O - I_O\exp(-\alpha CL) \approx \lambda CLI_0 \quad (4)$$

Therefore, the velocity v of the gas flow in the conduit 11 is:

$$v \propto (\Delta P_2 - \Delta P_1) \propto C \quad (5)$$

Thus, with the aid of the heat wire elements 12 and 13, an electrical signal E proportional to the gas density C can be obtained.

Now, the arrangement and the operating principle of the single-beam type infrared analyzer will be described with reference to FIG. 3. In FIG. 3, parts corresponding functionally to those which have been described with reference to FIG. 2 are designated by the same reference numerals or characters. The measurement beam IM emitted by light source 2 is partially absorbed by the first component gas in the measurement cell 4, and reaches a detector 25. The detector 25 comprises: a first detecting chamber (front chamber) 26 and a second detecting chamber (rear chamber) 27 which are arranged in the direction of the optical path of the measurement beam IM and filled with the first component gas; and a passage 28. That is, the detector is a serial-double-chamber type detector in which the measurement beam Im is partially absorbed in the first detecting chamber 26 and then absorbed in the second detecting chamber 27. The difference between the pressure increments which are caused by the absorption of the measurement beam in the first and second detecting chambers 26 and 27 is converted into an electrical signal by the heat wire elements 12 and 13 provided in the passage 28. In FIG. 3, reference numerals 16, 19, 21, 29 and 30 designate light transmitting windows.

It is assumed that the optical path lengths of the first and second detecting chambers 26 and 27 are represented by $L_2$ and $L_3$, respectively, the volumes of the chambers 26 and 27 are by $V_1$ and $V_2$, respectively, the density of the gas sealed in the detector is represented by $C_O$, the measurement cell incident light flux is represented by $I_O$, the measurement cell length is represented by L, the measurement cell transmission factor of the measurement beam IM which depends on the degree of any light absorbant coating (e.g., dust, soot etc.) of the inner wall of the measurement cell 4 is represented by T, and the density of the first component gas is represented by C. Then, the amounts of optical energy $\Delta I_2$ and $\Delta I_2$ which are absorbed in the first and second detecting chambers 26 and 27 are as follows:

$$\Delta I_1 = I_0 T \exp(-\alpha CL) \cdot \{1 - \exp(-\alpha C_0 L_2)\} \quad (6)$$

$$\Delta I_2 = I_0 T \cdot \exp(-\alpha CL) - \alpha C_0 L_2) \cdot \{1 - \exp(-\alpha(C_0 L_3))\} \quad (7)$$

The pressure increments $\Delta P_1$ and $\Delta P_2$ in the first and second detecting chambers are:

$$\Delta P_1 = K(\Delta I_1/V_1) \quad (8)$$

$$\Delta P_2 = K(\Delta I_2/V_2)$$

where K is the constant.

Therefore, the velocity v of the gas flow in the passage 28 is:

With $V_1 = V_2$, (9)

$$v \propto (\Delta P_1 - \Delta P_2) \propto (\Delta I_1/V_1 \Delta I_2/V_2)$$

$$\propto I_0 T \cdot \exp(-\alpha CL) \approx I_0 T(1 - \alpha CL)$$

Thus, with the aid of the elements 12 and 13, an electrical signal corresponding to the density C of the first component gas can be obtained.

As is apparent from the expressions (4) and (9), in the conventional gas analyzers shown in FIGS. 2 and 3, the zero point and the span point change with intensity of the measurement beam IM. Therefore, conventional gas analyzers suffer from a difficulty that measurement errors are caused by dust included in the gas 100 to be measured or by dust on the wall 31 of the measurement cell 4 or the light transmitting windows 19 and 21. In order to eliminate this difficulty, conventional analyzers employ a gas sampling system in which, when a gas 100 to be measured is introduced into the measurement cell from a measurement point such as a flue, a dust filter or the like is used to remove dust from the gas. That is, heretofore, a conventional gas analyzing system employed a gas sampling system so that the measurement would not be significantly affected by the dust in the gas being measured. However, such a method is still disadvantageous because of the following features: It is necessary to periodically replace the filter or to periodically calibrate the instruments; that is, it is necessary to perform maintenance for the analyzer periodically. Furthermore, because it takes a relatively long time to lead the gas to be measured from the measurement point to the measurement cell 4, the response speed of the analyzer is low. Therefore, the analyzer is not applicable to a technical field such as combustion control in which a high speed response is essential. On the other hand, a gas filter correlation type (GFC type) infrared analyzer and an infrared dual-channel type analyzer have been proposed as infrared analyzers which are not affected by variations in the light flux. However, the GFC type infrared analyzers is low in both durability and in reliability, because it is necessary to turn the gas filter at high speed. The infrared dual-channel type analyzer is also disadvantageous in that it is expensive because an infrared tunable laser is employed as its light source.

Accordingly, it is an object of this invention to provide an infrared analyzer in which the above-described difficulties accompanying a conventional infrared analyzer have been eliminated, and which is applicable to combustion control or the like because of it being sufficiently high in response speed. An additional object of the present invention is to be low in operation cost and free of maintenance. A further object of the invention is to provide an infrared analyzer in which the measurement result is not affected by coatings on the interior measurement cell due to solids in the material under measurement which contains the particular component to be measured. In addition, it is a further object of the invention that the analyzer neither be affected by the second component which coexists with the particular component in the material under measurement and has an infrared ray absorbing wavelength band different from that of the particular component.

SUMMARY OF THE INVENTION

In order to achieve the foregoing objects of the invention, there is provided an infrared analyzer that has a source of infrared radiation. A measurement call receives the material to be analyzed and transmits the infrared radiation therethrough the material which contains a first component which absorbs infrared radiation of the first wavelength and second component which absorbs infrared radiation of a second wavelength. The combination further includes an infrared detecting means which is comprised of several components. A first detector for measuring the amount of infrared radiation which is absorbed by the first component. The first detector generates a first detector output signal. An optical filter for absorbing the infrared radiation of the second wavelength is interposed between the first detector and a second detector. The second detector measures the amount of infrared radiation passed through the first detector and the optical filter. The second detector generates a second detector output signal. The infrared analyzer further comprises means for using the first and second detector output signals to determine the concentration of the first component in the material. Preferably, the analyzer includes a means for focusing infrared radiation on the second detector. It is also preferred that the optical filter include water. It is further preferred that the analyzer include means for collimating the infrared radiation passing through the measurement cell.

Embodiments of the present invention are illustrated in the attached figures which form a part of the present specification.

DESCRIPTION OF THE PREFERRED EMBODIMENTS

Figure 3:
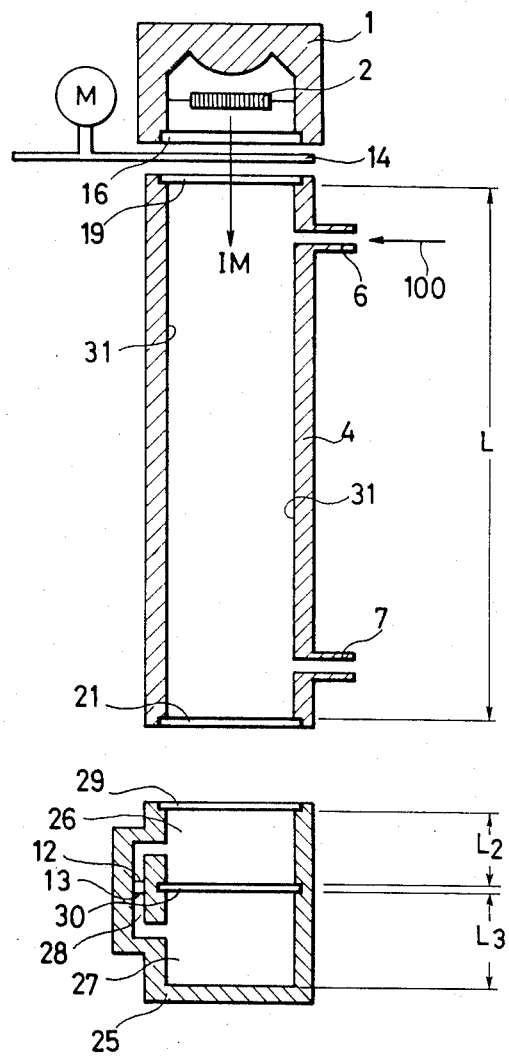
FIG. 3 is a schematic cross-sectional view of a conventional single-beam gas analyzer.
Figure 4:
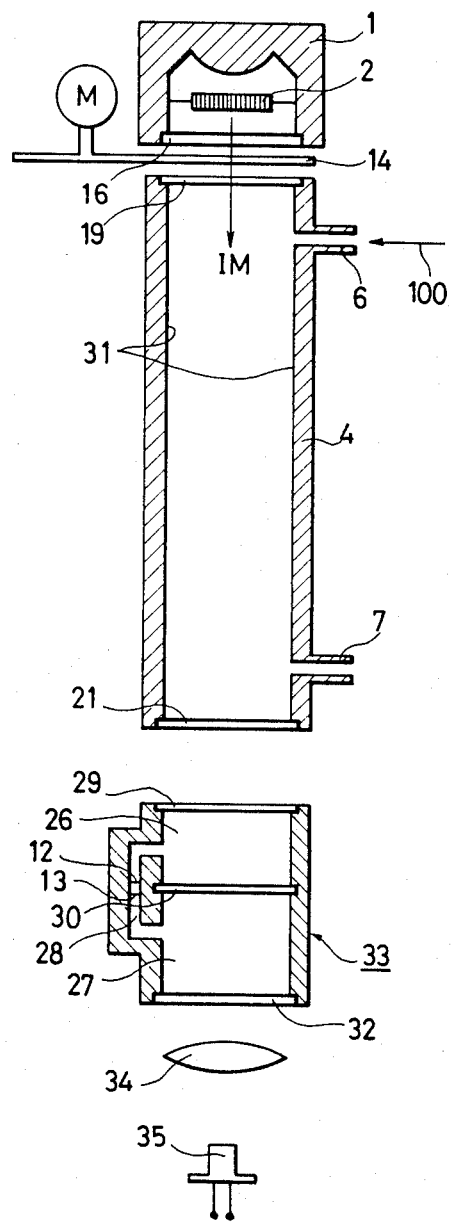
FIG. 4 is a schematic cross-sectional view of a conventional single-beam gas analyzer used to describe the principles of operation of the present invention.

Before description of the embodiments of this invention, the principle of the invention will be described. FIG. 4 is a cross-sectional schematic diagram that will be used to describe the principle of the invention. An infrared analyzer shown in FIG. 4 is different from that shown in FIG. 3 in that the former has a gas-sealed detector 33 (or a first detector) with a light transmitting window 32, an infrared lens 34 made of calcium fluoride or sapphire, and an infrared detector 35 (or a second detector). The infrared detector 35 may be a thermopile, a current collection type detector, a thermistor bolometer, a photoconductive cell, a photovoltaic detector, or a Golay cell. The gas sealed detector 33 can be obtained by replacing the bottom of the detector 35 of FIG. 3 with the window 32. The measurement beam IM passed through the measurement cell 4 exists through the window 32 after the energy is absorbed in the first and second detecting chambers 26 and 27. The infrared lens 34 is so arranged that the beam emerging through the window 32 is focused on the infrared detector 35 having a small light receiving area.

The infrared analyzer of FIG. 4 is constructed as described above. The intensity (Im) of the measurement beam IM emerging from the measurement cell 4 is equal to $I_0$ ($Im = I_0 T$). Therefore, the output (E) of the gas-sealed detector 33 is as follows:

From the expression (9).

$$E \propto v \propto Im(1 - \alpha CL) \qquad (10)$$

Figure 5:
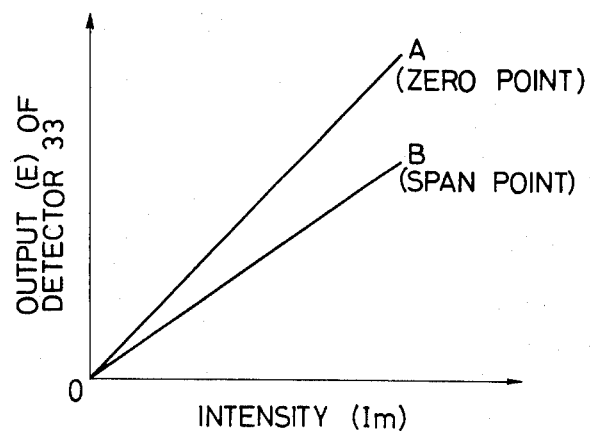
FIG. 5 and 6 are all graphs illustrating principles applicable to the present invention.

It can be understood from FIG. 5 that, if the quantity of light (Im) passed through the measurement cell is measured and the measurement signal is utilized to compensate for the detector output E, then it is possible to provide an analyzer in which no measurement error occurs even when the quantity of light changes. Based on this fact, the invention is intended to use the infrared detector 35 to compensate for measurement error which occurs with variation in the quantity of light.

The output E of the detector 33 corresponds to the absorption of infrared rays which is carried out in a first wavelength band by the first component gas sealed in the detector 33. On the other hand, the infrared detector 35 is sensitive to infrared rays in a wide range of wavelengths, and therefore, the output V of the detector 35 is scarcely affected by the absorption of infrared rays which is carried out by the first component gas in the detector 33 having a narrow absorption wavelength band; that is, it corresponds to the infrared intensity Im. This value changes as the transmission factor T is changed because of contamination of the measurement cell 4 for instance, as was described above. Accordingly, if the beam emergent from the measurement cell 4 is detected by the detector 35, and its detection result is used together with the detection result of the detector 33, then the first component gas density C can be correctly obtained even when the measurement cell 4 is dirty.

Figure 6:
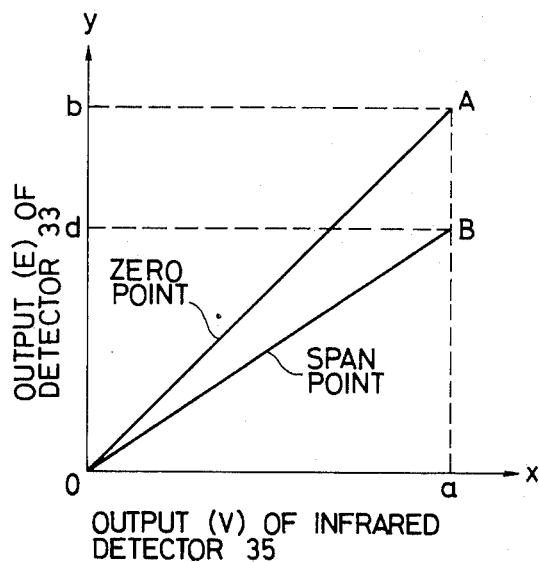

A method of using the detection outputs of the detectors 33 and 35 to obtain the density C will be described. As was described before, the output V of the detector 35 is proportional to the quantity of light Im. Therefore, the output x of the detector 35 and the output y of the detector 33 relate to each other as indicated in FIG. 6 which is obtained by referring to FIG. 5. In FIG. 6, the points A and B are the zero point and the span point, respectively, when the measurement cell 4 is clean; that is, the transmission factor T=1. Further in FIG. 6, reference character a denotes the value of the abscissa of the points A and B, respectively. At the point O, the measurement beam IM is completely intercepted, and the outputs of the detectors 33 and 35 are zero. Therefore, the following relation is established between (b-d) and (c):

$$b - d = k_1 C \qquad (11)$$

where $K_1$ is the proportional constant.

When the measurement cell 4 becomes contaminated so that the quantities of light applied to the detectors 33 and 35 are affected, the zero point and span point outputs of the detectors 33 and 35 change according to the straight lines AO and BO, respectively. Therefore, in the case of a single-beam type infrared analyzer, the following relation is established between the output x of the detector 35 and the output y of the detector 33:

$$y = \frac{d}{a} x \qquad (12)$$

The expression (12) can be rewritten as follows:

$$d = \frac{ay}{x} \qquad (13)$$

Therefore, by using the output x of the infrared detector and the output y of the dectector 33, d can be obtained. Accordingly, the gas density C can be obtained from the following equation (14):

$$C = \frac{b - d}{k_1} = \frac{b}{k_1} - \frac{ay}{k_1 x} \qquad (14)$$

The infrared analyzer shown in FIG. 4 is used to perform the measurement without being affected by the contamination of the measurement cell 4.

Figure 1:
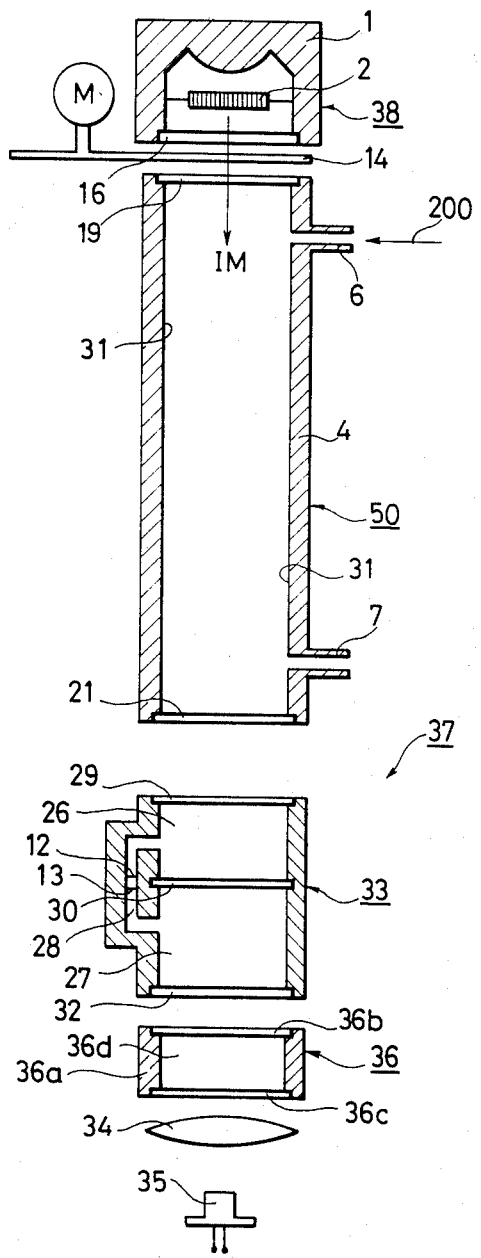
FIG. 1 is a schematic cross-sectional view of an embodiment of the invention.

FIG. 1 shows the arrangement of one embodiment of this invention. An infrared analyzer of FIG. 1 is different from that of FIG. 4 in that the former has an optical filter 36 between the gas-sealed detector 33 and the infrared lens 34. The optical filter 36 is formed by sealing both ends of a cylindrical case 36a with infrared transmitting windows 36b and 36c which are made of the same material as the window 19 of the measurement cell 4, and by filling the inside with a filler 36d, such as water. The filler 36d may be of any aqueous solution.

The optical filter 36 may be made of quartz glass or synthetic glass containing hydroxyl group (OH group).

FIG. 1, depicts an infrared analyzer 37 comprised of the above-described components. A material to be measured 200 (e.g., burnt exhaust gas) is introduced through the conduit 6 into the measurement cell 4 and discharged through the conduit 7. The analyzer 37 may be used to measure the density of carbon monoxide (CO) in the exhaust gas 200.

In the infrared analyzer 37, an infrared source section 38 comprising the light source chamber 1, the light source 2 and the window 16 emits the measurement beam IM. When the measurement beam IM thus emitted is applied to the measurement cell 4, it is intermittently intercepted by the rotor 14 which is driven by the motor M. In FIG. 1, a measurement cell section 50 is comprised of the measurement cell 4, the conduits 6 and 7, and the windows 19 and 21. The measurement beam IM thus applied to the measurement cell 4 while being intermittently intercepted is treated as follows: That is, its optical energy in the first wavelength band $\lambda 1$, the inherent wavelength band of the CO gas included as the first component gas in the exhaust gas 200, is partially absorbed by the CO gas according to the density of the latter gas, and almost all the remaining part of the infrared energy in the wavelength band $\lambda_1$ is absorbed by the gas-sealed detector 33. Therefore, the output E of the detector 33 corresponds to the CO density of the exhaust gas 200. The measurement beam IM passed through the detector 33 is applied through the optical filter 36 and the lens 34 to the infrared detector 35. Accordingly, the infrared beam applied to the detector 35 is such that almost all the energy in the second wavelength band $\lambda 2$ which is the inherent wavelength band of water has been absorbed. Therefore, in this case, the output V of the detector 35 is not related to the steam density of the exhaust gas 200 at all in the case where the exhaust gas 200 introduced into the measurement cell 4 contains CO gas and steam but no other components which absorb infrared energy greatly. The output V is not affected by the CO density, as was described before.

Figure 7:
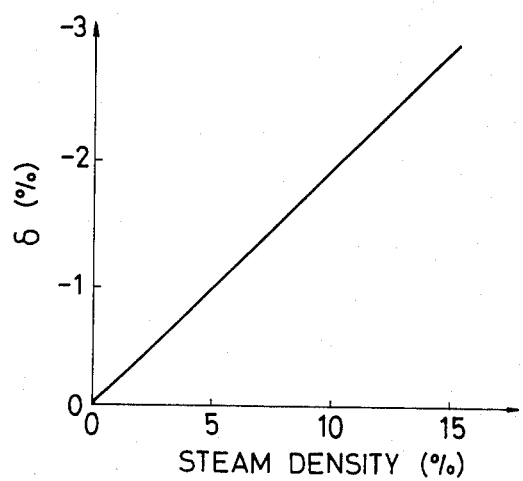
FIG. 7, 8 and 9 are graphs illustrating the results of experiments using embodiments of the present invention.

The infrared analyzer 37 is used to determine a CO density C according to the expression (14). Therefore, if the optical filter 36 is not used, a measurement error occurs, because the output of the infrared detector 35 changes when the steam density of the exhaust 200 changes. FIG. 7 is an explanatory diagram showing experimental results on the output variation $\delta$ of the detector 35 which is caused when the optical filter 36 is not used. As is apparent from FIG. 7, when the steam density of the exhaust gas 200 is 10(%), the output of the detector 35 changes about $-2(\%)$. If the optical filter 36 is eliminated from the analyzer 37, then a measurement error occurs with the variation of the steam density; however, the frequency of occurrence of such an error has been decreased by the provision of the filter 36.

Figure 10:
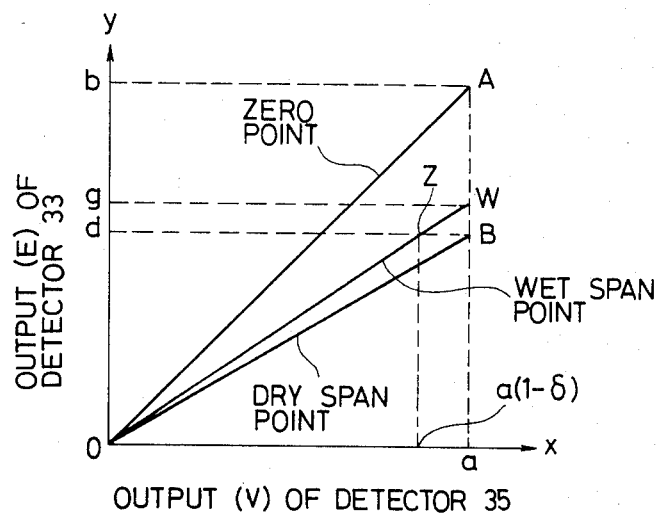
FIG. 10 is a graph illustrating the source of measurement errors.

Now, the aforementioned measurement error will be described in more detail. FIG. 10 is an explanatory diagram for a description of the relation between the output E of the detector 33 and the output V of the detector 35 in the analyzer 37. In FIG. 10, reference character A designates the zero point provided when the measurement cell 4 is clean; B, the span point provided when no steam is contained in the exhaust gas 200 (hereinafter referred to as "a dry span point", when applicable); and W, the span point provided when steam is contained in the exhaust gas (hereinafter referred to as "a wet span point", when applicable). Further in FIG. 10, reference character a designates the value of the abscissa of the points A, B and W, and b, q and d, the values of the ordinates of the points A, W and B, respectively. If, when CO gas having the span density and steam having an optical density are contained in the exhaust gas 200, the optical filter 36 is eliminated from the analyzer 37, then as shown in FIG. 10, the output V of the infrared detector 35 becomes a $(1-\delta)$ which is smaller by $(\delta \cdot a)$ than a, and the output E of the gas-sealed detector 33 becomes d. In FIG. 10, the abscissa of the point Z is $(1-\delta)$, and the ordinate is d, and the point W is on the extraparater of the line oz. As was described before, the expression (14) is obtained from FIG. 6. The following expression (15) is obtained from the characteristic line OW in FIG. 10:

$$Y = (g/a)x \qquad (15)$$

The density $C_1$ provided when the expression (15) is inserted in the expression (14) is:

$$C_1 = (b - g)/k_1 \qquad (16)$$

On the other hand, the characteristic line OW in FIG. 10 can be expressed as follows:

$$y = [d/\{a(1 - \delta)\}] \cdot x \approx (d/a)(1 + \delta) \cdot x \qquad (17)$$

The following expression (18) can be obtained through comparison of the expressions (15) and (17), and the following expression (19) can be obtained from the expressions (16) and (11);

$$g = d(1 + \delta) \qquad (18)$$

$$\frac{C_1 - C}{C} = \frac{-d \cdot \delta}{b - d} = \frac{\Delta C}{C} = e \qquad (19)$$

where $\Delta C = C_1 - C$.

The following equation (20) is obtained from the expression (19):

$$e = \frac{-(d/b)}{1 - (d/b)} \cdot \delta \qquad (20)$$

Figure 8:
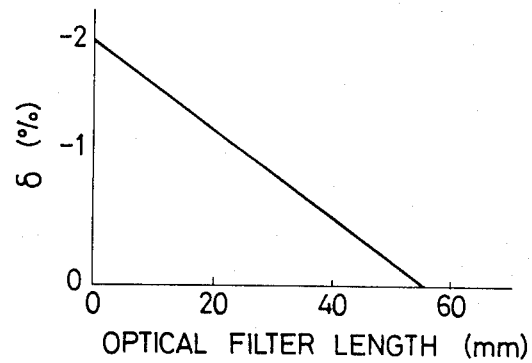
Figure 9:
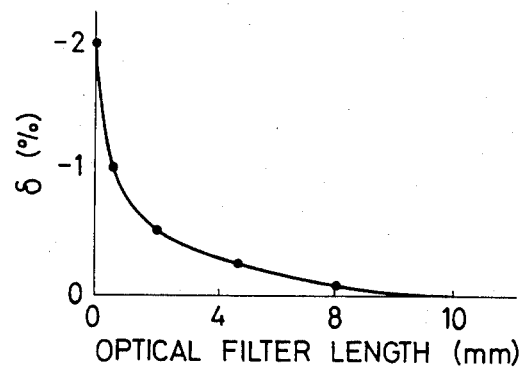

It is apparent from the equation (2) that the measurement error e of the infrared analyzer 37 is $(d/b)/\{1-(d/b)\}$ times as large as the output variation factor $\delta$ of the infrared detector 35. In general, in a burnt exhaust gas, the steam density varies about 10%. If, in this case, the optical filter 36 is not used, then the output of the infrared detector 35 changes about $-2\%(=\delta)$. Generally, $d/b = 0.8$. Therefore, with $\delta = -2$ and $d/b = 0.8$, $e = -8(\%)$. That is, if the optical filter 36 is eliminated from the analyzer 37, in the measurement of the CO density of the exhaust gas 200 a measurement error of the order of 8% is caused by the steam in the exhaust gas. In general, in the case where combustion control is carried out by using an infrared analyzer, the measurement error e should be not more than $\pm 2\%$. Accordingly, in this case, it is necessary from the equation (20) that $\delta = \pm 0.5\%$ or less with $d/b = 0.8$ and $e = 2$. FIG. 8 is a diagram showing experimental results provided when the optical filter is made of quartz glass. FIG. 9 is also a diagram showing experimental results provided when the optical filter 36 has water as its filter 36d. It is apparent from FIGS. 8 and 9 that δ becomes 0.5% or less when, in the case of FIG. 8, the length of the filter is set to 40 mm or more, and in the case of FIG. 9, the length of the filter is set to 2 mm or more. Therefore, in the infrared analyzer 37 of FIG. 1, the infrared transmission optical path length of the filter 36 is set to 40 mm or more in the case where the filter is made of quartz glass, and to 2 mm or more in the case where the filter's filler is water.

Figure 11:
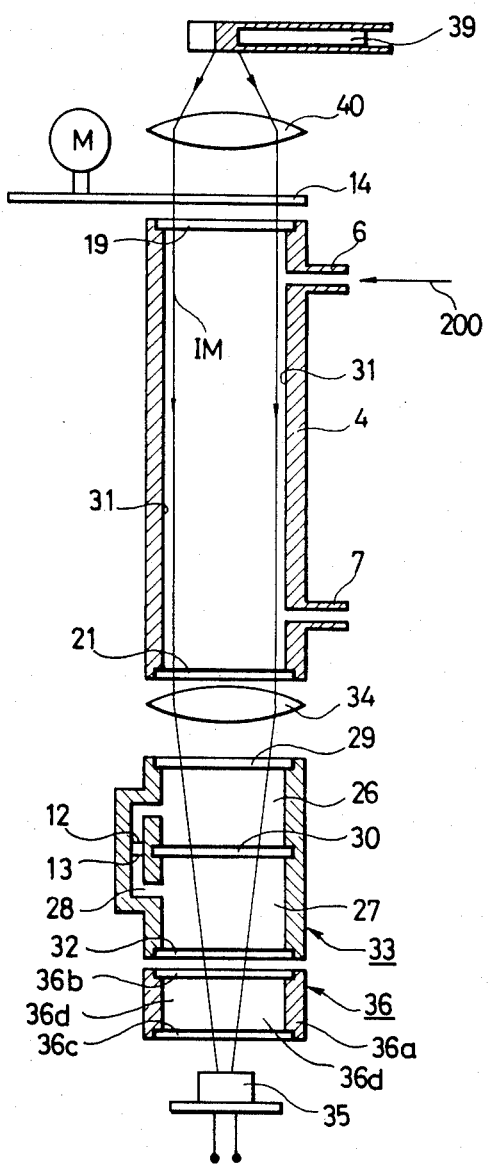
FIG. 11 is a schematic cross-sectional view of a single-beam gas analyzer embodiment of the present invention.

FIG. 11 is a diagram showing the arrangement of a second embodiment of the invention. An infrared analyzer of FIG. 11 is different from that of FIG. 1 mainly in that the former analyzer has an infrared source 39 which emits infrared rays radially, and an infrared lens 40 for making the infrared rays parallel so that the infrared rays are applied to the measurement cell 4 in parallel with the axis of the measurement cell. In this case, the infrared lens 40 is made of the same material as the aforementioned infrared lens 34. The infrared lens 34 is arranged so that the parallel infrared rays passed through the measurement cell 4 are focused on the infrared detector 35 through the gas-sealed detector 33 and the optical filter 36. In the analyzer of FIG. 11, the optical path of the infrared passing through the measurement cell 4 is parallel with the axis of the cell 4, as was described above. Therefore, the intensity of the infrared beam emerging from the measurement cell 4 is scarcely affected by any contamination of the measurement cell's inner wall 31 which is due to the dust in the exhaust gas 200. Accordingly, the variation of the infrared transmission factor T in the measurement cell 4 is small, and therefore, the measurement error is also small. Similarly as in the analyzer 37 of FIG. 1, the analyzer of FIG. 11 has the optical filter 36. Therefore, when the analyzer of FIG. 11 is used to measure the CO density of the exhaust gas, the measurement error attributing to the steam is also small.

Figure 12:
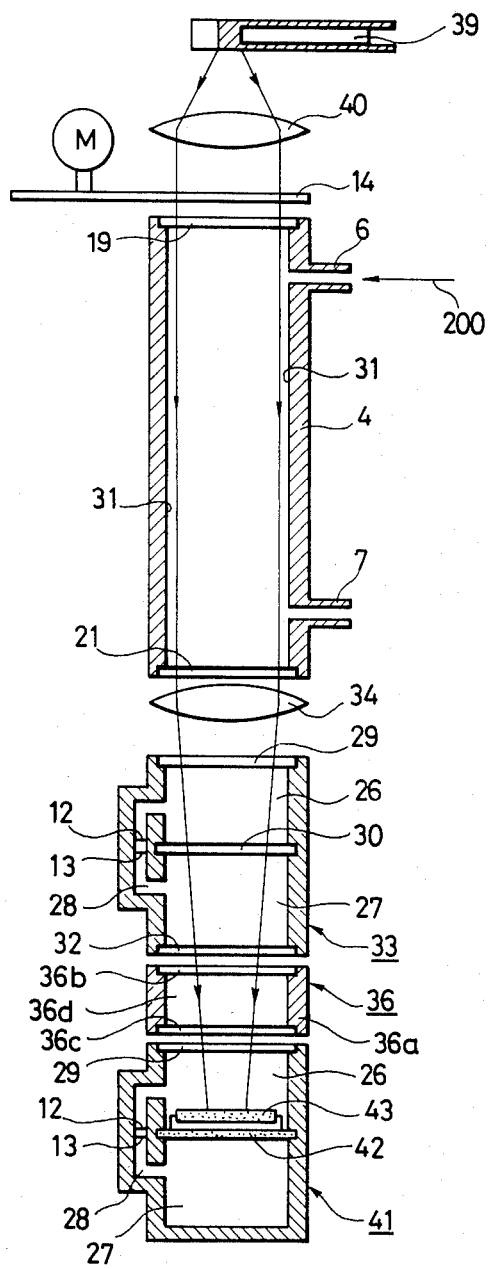
FIG. 12 is a schematic cross-sectional view of another single-beam gas analyzer embodiment of the present invention.

FIG. 12 is a diagram showing the arrangement of a third embodiment of the invention. An infrared analyzer shown in FIG. 12 is different from the infrared analyzer of FIG. 11 in that, instead of the infrared detector 35 of FIG. 11, an infrared detector 41 is provided. The infrared detector 41 is substantially similar in construction to the detector 25 shown in FIG. 3; however, a partition wall 42 which intercepts infrared rays is provided at the position wall of window 30 of the detector 25, and an infrared absorbing element 43 is provided above the partition wall 42. The gas such as nitrogen gas which absorbs no infrared rays is sealed in the detector 41. The detector 41 is so disposed that the infrared rays passing through the gas-sealed detector 33 and the optical filter 36 are focused on the infrared absorbing element 43 by the infrared lens 34. Therefore, the temperature of the infrared absorbing element 43 is increased by the infrared rays thus focused, so that the pressure in the first detecting chamber 26 of the detector 41 is increased. Similarly as in the infrared detector 35 of FIG. 11, the infrared absorbing element 43 is adapted to absorb infrared rays in a wide range of wavelengths. Therefore, the output of the detector 41 corresponds to the intensity of infrared rays applied to the detector 41. Thus, as in the case of the analyzer of FIG. 11, the CO density of the exhaust gas 200 can be measured without being affected by the variation of the infrared transmission factor in the measurement cell 4 and the variation of the quantity of steam in the exhaust gas 200.

Figure 2:
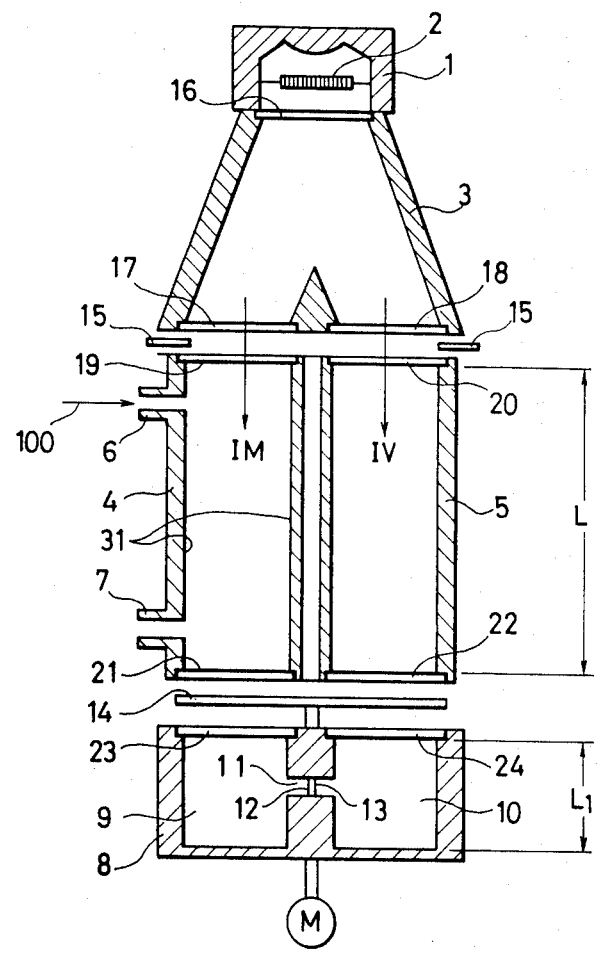
FIG. 2 is a schematic cross-sectional view of a conventional double-beam gas analyzer.
Figure 13:
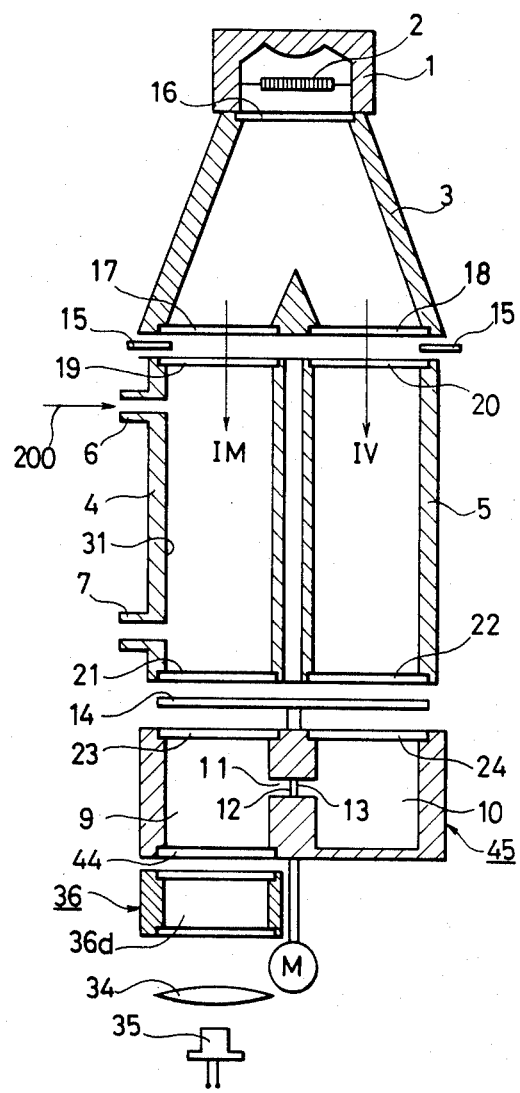
FIG. 13 is a schematic cross-sectional view of a double-beam gas analyzer embodiment of the present invention.

FIG. 13 is a diagram showing the arrangement of a fourth embodiment of the invention. An infrared analyzer of FIG. 13 is different from the infrared analyzer of FIG. 2 in the following points: A gas-sealed detector 45, which is similar in construction to the detector 8 of FIG. 2 except that an infrared ray transmitting window 44 is formed in the bottom of the first detecting chamber 9, is provided as the first detector, and the analyzer is so designed that the measurement beam IM emerging from the measurement cell 4 is applied to the first detecting chamber 9 and applied to the infrared detector 35 through the window 44, the optical filter 36 and the lens 34. In this case, the detector 45, the filter 36, the lens 34, and the detector 35 are arranged similarly as in the case of detector 35 of FIG. 1. In this case, as is apparent from the equation (4), the output F of the detector 45 is as follows:

$$F \propto \alpha CLTI_O = \alpha CLI_m \qquad (21)$$

Where T is the infrared transmission factor in the measurement cell 4.

As was described before, the output V of the detector 35 is proportional to the quantity of incident infrared rays. Therefore, if the optical filter 36 is eliminated, then the output V corresponds to the infrared intensity IM. Therefore, when the optical filter 36 is not used, if the output F of the detector 45, and the output V of the detector 35 are employed, then according to the expression (21) the CO gas density, the first component gas, in the exhaust gas 200 can be measured without being affected by the variation of the infrared transmission factor T. However, the result of measurement in this case includes an error, because when the stream density of the exhaust gas 200 changes, the output V of the detector 35 changes even if the output F of the detector 45 is maintained unchanged. However, in the fourth embodiment of FIG. 13, the filter 36 is employed, and therefore the CO gas density can be measured without being affected by the quantity of steam.

As was described above, the optical filter 36 intercepts the infrared component in the second wavelength band $\lambda_2$ of the infrared rays applied to the infrared detectors 35 and 41 so that the infrared component is not applied to the detectors. The second wavelength band $\lambda_2$ is different from the first wavelength band $\lambda_1$ of infrared rays which are absorbed by the gas sealed in the detector 33 and 45. Therefore, in the above-described embodiments, the filter 36 is disposed between the detectors 33 and 35, 33 and 41, or 45 and 35; however, it goes without saying that the filter 36 may be positioned between the measurement cell 4 and the detector 33 or 45. Each of the above-described wavelength bands $\lambda_1$ and $\lambda_2$ may consist of a single wavelength band or a plurality of wavelength bands.

Furthermore, in the above-described embodiments, the water filter or quartz filter is employed because the measurement of the CO density of the exhaust gas is interrupted by the steam therein. It should, be noted, however, that the invention is not limited thereto. In the case where the gas to be measured contains the first component gas which absorbs infrared rays in the first wavelength band and the second component gas which absorbs infrared rays in the second wavelength band different from the first wavelength bands, the optical filter 35 is made of solid, liquid or gas so as to intercept the infrared rays in the second wavelength band. In the above-described embodiment, the material to be measured is exhaust gas and the density of the CO gas, the first component of the material is measured. The invention is not limited thereto and the material to be measured by the inventions may be liquid or solid.

The present invention has been disclosed in terms of several embodiments and the invention is not limited thereto. The scope of the present inventions is determined by the appended claims and their equivalents.

What is claimed is:

1. An infrared analyzer comprising;
   a source of infrared radiation;
   a measurement cell for receiving material to be analyzed and transmitting said radiation therethrough, said material containing a first component which absorbs infrared radiation of a first wavelength and a second component which absorbs infrared radiation of a second wavelength;
   an infrared detecting means, said detecting means including
      a first detector, said first detector comprising a first detecting chamber and a second detecting chamber, said detecting chambers having different path lengths, said first detector measuring the amount of infrared radiation absorbed by said first component and generating a first detector output signal;
      an optical filter for absorbing infrared radiation of said second wavelength;
      a second detector, sensitive to infrared radiation in the wavelengths other than said first wavelength and said second wavelength, said second detector measuring the amount of infrared radiation passed through said first detector and said optical filter and generating a second detector output signal; and
   means for using the first and second detector output signal to determine the concentration of said first component in said material.

2. The analyzer of claim 1 wherein said analyzer includes means for focusing infrared radiation to said second detector.

3. The analyzer of claim 1 wherein said optical filter includes water.

4. The analyzer of claim 1 wherein said optical filter contains an aqueous solution.

5. The analyzer of claim 1 including means for collimating said infrared radiation passing through said measurement cell, said collimating means being disposed to direct said radiation parallel to the axis of said measurement cell.

6. An infrared analyzer comprising:
   a source of infrared radiation;
   a measurement cell adapted to receive material to be analyzed wherein said material contains a first component which absorbs infrared radiation of a first wavelength and a second component which absorbs infrared radiation of a second wavelength and to transmit said radiation therethrough;
   a reference cell adapted to contain a gas non-absorptive of infrared radiation;
   an infrared detection means including
      a first detector, said first detector having a first detector section adapted to measure the amount of infrared radiation absorbed by said first component and a second detector section adapted to measure the amount of infrared radiation absorbed by said gas non-absorptive of infrared radiation, wherein a first portion of infrared radiation passes through said measuring cell into said first detector section and a second portion of infrared radiation passes through said reference cell into said second detector section, said first detector generating a first output signal corresponding to infrared radiation measured thereby;
      an optical filter adapted to absorb infrared radiation of said second wavelength;
      a second detector, sensitive to infrared radiation having wavelength other than said first wavelength and said second wavelength, adapted to measure the amount of infrared radiation passed through said first detector section and said optical filter, said second detector generating a second detector output signal corresponding to the infrared radiation measured thereby; and
   means for using the first and second detector output signals to determine the concentration of said first component in said material.

* * * * *